US00PP30158P2

(12) United States Plant Patent
Kleinwee

(10) Patent No.: US PP30,158 P2
(45) Date of Patent: Jan. 29, 2019

(54) ***OSTEOSPERMUM* PLANT NAMED 'OSTZ0009'**

(50) Latin Name: *Osteospermum ecklonis*
Varietal Denomination: OSTZ0009

(71) Applicant: SYNGENTA PARTICIPATIONS AG, Basel (CH)

(72) Inventor: Theodorus Cornelis Maria Van Kleinwee, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,592

(22) Filed: Jul. 6, 2017

(51) Int. Cl.
*A01H 5/02* (2018.01)

(52) U.S. Cl.
USPC ..... Plt./360

(58) Field of Classification Search
USPC ..... Plt./360
See application file for complete search history.

*Primary Examiner* — Susan McCormick Ewoldt
(74) *Attorney, Agent, or Firm* — Dale Skalla

(57) ABSTRACT

A new *Osteospermum* plant named 'OSTZ0009' particularly distinguished by the yellow flowers and long peduncles.

1 Drawing Sheet

Latin name of the genus and species of the plant claimed: *Osteospermum ecklonis.*

Varietal denomination: 'OSTZ0009'.

BACKGROUND OF THE NEW PLANT

The present invention comprises a new and distinct cultivar of *Osteospermum*, botanically known as *Osteospermum ecklonis* (DC.) Norl., and hereinafter referred to by the cultivar name 'OSTZ0009'.

'OSTZ0009' is a product of a planned breeding program. The new cultivar has a large number of medium sized, yellow flowers, is freely branching, has medium vigor and is very floriferous throughout the season.

'OSTZ0009' originated from open pollination made in the summer of 2011 in Enkhuizen, The Netherlands. The female parent was an unpatented, proprietary *Osteospermum* plant designated 'P0439-1', having bigger flowers with deeper yellow color.

The male parent of 'OSTZ0009' is a variety named 'Balvoyelo' (U.S. Plant Pat. No. 21,122) that has lighter yellow flowers and smaller flower size with longer peduncles.

The resulting seeds were sown in January 2012 in Enkhuizen, The Netherlands. 'OSTZ0009' was selected as one flowering plant within the progeny of the stated cross in May 2012 in a controlled environment in Enkhuizen, the Netherlands.

The first act of asexual reproduction of 'OSTZ0009' was accomplished when vegetative cuttings were propagated from the initial selection in the summer of 2012 in a controlled environment in Angers, France.

BRIEF SUMMARY OF THE INVENTION

Horticultural examination of plants grown from cuttings of the plant initiated in the summer of 2012 in Angers, France, and continuing thereafter, has demonstrated that the combination of characteristics as herein disclosed for 'OSTZ0009' are firmly fixed and are retained through successive generations of asexual reproduction. 'OSTZ0009' has not been observed under all possible environmental conditions.

The phenotype may vary significantly with variations in environment such as temperature, light intensity and day length.

A Plant Breeder's Right for this cultivar has not been applied for. 'OSTZ0009' has not been made publicly available prior to the effective filing date of this application, notwithstanding any disclosure that may have been made less than one year prior to the effective filing date of this application by the inventor or another who obtained 'OSTZ0009' directly from the inventor.

The following traits have been repeatedly observed and are determined to be basic characteristics of the new variety. The combination of these characteristics distinguishes this *Osteospermum* as a new and distinct variety.

DESCRIPTION OF THE PHOTOGRAPHS

The accompanying photograph drawing shows typical flower and foliage characteristics of 'OSTZ0009' with colors being as true as possible with an illustration of this type.

Figure 1:
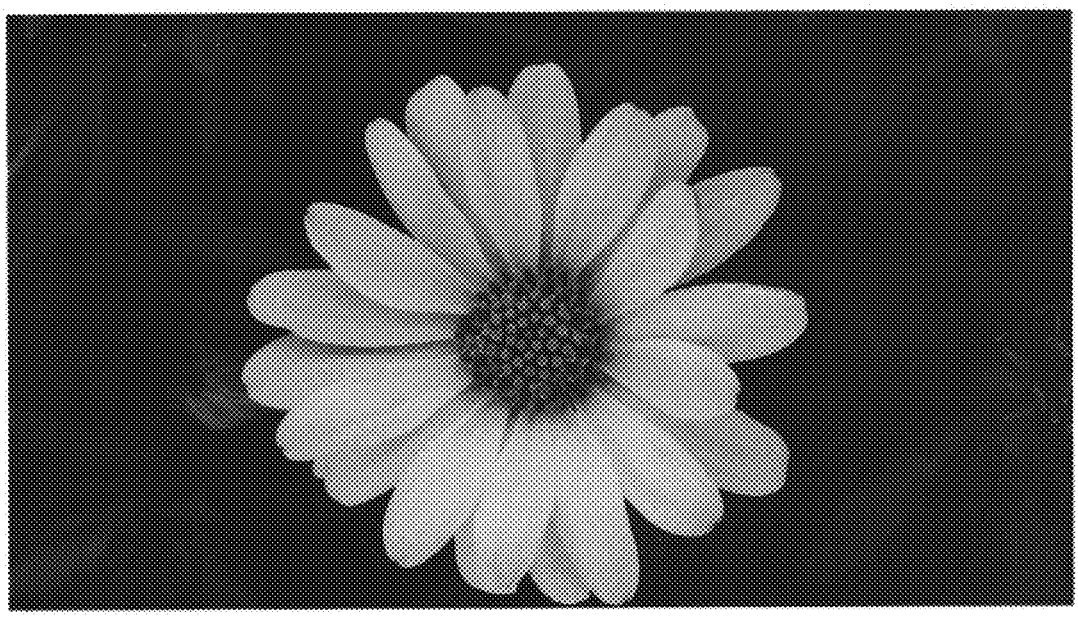

The photograph drawing shows in FIG. 1 a close-up of the flowers, and in

Figure 2:
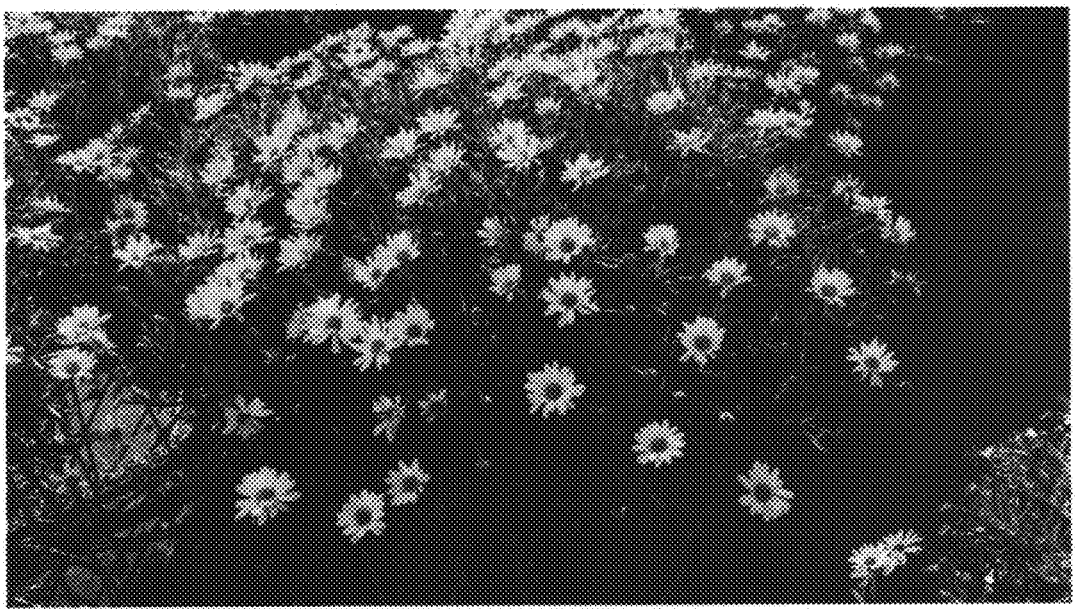

FIG. 2 a flowering potted plant of the new variety.

DETAILED BOTANICAL DESCRIPTION

The aforementioned photographs were taken in April 2015 from plants grown in a greenhouse trial in Enkhuizen, The Netherlands. These plants were grown in 10.5 cm pots and were approximately 14 weeks of age. The close-up photograph was taken at the same time.

The observations and measurements were taken in Enkhuizen, The Netherlands in October 2016 on about 23 week old plants that were growing outdoors in 25 cm pots.

Color references are made to The Royal Horticultural Society Colour Chart (R.H.S.), 2001.

TABLE 1

DIFFERENCES BETWEEN THE NEW VAREITY 'OSTZ0009' AND A MOST SIMILAR VARIETY

| | 'OSTZ0009' | 'Oste Yel' (U.S. Plant Pat. No. 19,050) |
|---|---|---|
| Flower size: | Medium size | Larger |
| Internode length: | Shorter | Longer |
| Quantity of Inflorescences: | More | Less |

Plant:
- *Plant height.*—15 cm.
- *Plant height (inflorescence included).*—25 cm.
- *Plant width.*—40 cm.

Foliage:
- *Arrangement.*—Alternate, simple.
- *Immature leaf, color upper surface.*—RHS 137C.
- *Immature leaf, lower surface.*—RHS 137D.
- *Mature, leaf color, upper surface.*—RHS 137C.
- *Mature leaf, lower surface.*—RHS 137D.
- *Length.*—5.0 cm.
- *Width.*—0.6-1.0 cm.
- *Shape.*—Oblanceolate.
- *Base shape.*—Attenuate.
- *Apex shape.*—Acute.
- *Margin.*—Entire to slightly Spinose.
- *Texture, upper surface.*—Smooth, occasionally a short hair.
- *Lower surface.*—Very short hair, on margins and veins, only occasionally hairs on rest of lower surface.
- *Color of veins, upper surface.*—RHS 138B.
- *Color of veins, lower surface.*—RHS 138B.
- *Petiole color.*—RHS 138B.
- *Length.*—1.5 cm.
- *Diameter.*—0.3 cm.
- *Texture.*—Smooth, but some pubescence at margin.

Stem:
- *Quantity of main branches per plant.*—10-12.
- *Color of stem.*—RHS 138B, more brown at base.
- *Length of stem.*—20-25 cm.
- *Diameter.*—0.2-1.0 cm.
- *Length of internodes.*—0.5-1.3 cm.
- *Texture.*—Glabrous.
- *Color of peduncle.*—RHS 138B.
- *Length of peduncle.*—Up to 12 cm.
- *Peduncle diameter.*—0.3 cm.
- *Texture.*—Light Pubescent.

Inflorescence:
- *Quantity of inflorescences.*—80.
- *Lastingness of individual blooms on the plant.*—10 days.
- *Fragrance.*—None.

Bud (just when opening/showing color):
- *Color.*—RHS 14A with stripes RHS 187C.
- *Length.*—1.5 cm.
- *Width.*—1.5 cm.
- *Shape.*—Ovate.

Immature inflorescence:
- *Diameter.*—4 cm.
- *Color of ray florets.*—RHS 14B.

Mature inflorescence:
- *Diameter.*—5.5 cm.
- *Diameter of disc.*—1.2 cm.
- *Average quantity of ray florets.*—Approximately 19.
- *Average quantity of disc florets.*—Approximately 150.

Ray florets:
- *Color upper surface.*—RHS 14A.
- *Color lower surface.*—RHS 14A with stripes RHS 187C.
- *Length.*—3 cm.
- *Width.*—0.7 cm.
- *Shape.*—Oblanceolate.
- *Apex shape.*—Tridentate.
- *Margin.*—Entire.
- *Texture, upper surface.*—Glabrous.
- *Texture, lower surface.*—Base canescent.

Disc florets:
- *Color of florets.*—Base lighter than RHS 157D, RHS 9C towards top.
- *Length.*—0.7 cm.
- *Width.*—0.2 cm.
- *Shape.*—Tubular, elongated.
- *Apex shape.*—Acute, 5 pointed.
- *Corolla, tube color.*—RHS 9C, with tip RHS 187A.
- *Length.*—0.2 cm.
- *Width.*—0.2 cm.
- *Apex shape.*—Acute.
- *Base shape.*—Fused, attached petals jointed corolla lobs.
- *Margin.*—Entire.
- *Texture.*—Corolla base canescent.

Phyllaries:
- *Quantity.*—About 22.
- *Color, upper surface.*—RHS 138A.
- *Color, lower surface.*—RHS 138A.
- *Length.*—0.8-1.2 cm.
- *Width.*—0.2 cm.
- *Shape.*—Ligulate.
- *Apex shape.*—Acute.
- *Base.*—Fused.
- *Margin.*—Entire.
- *Texture.*—Pubescent on both sides.

Reproductive organs:
- *Pistil.*—1.
- *Length.*—0.1 cm.
- *Style color.*—RHS 22B, white at the base.
- *Style length.*—0.7 cm.
- *Stigma color.*—RHS 22A.
- *Stigma shape.*—Bipartite.
- *Stamens.*—Not observed.

What is claimed is:

1. A new and distinct variety of *Osteospermum* plant named 'OSTZ0009' substantially as illustrated and described herein.

* * * * *